(12) United States Patent
Sontyana et al.

(10) Patent No.: US 10,864,507 B2
(45) Date of Patent: Dec. 15, 2020

(54) METHOD FOR THE SYNTHESIS OF A ZSM-22 ZEOLITE, A METAL CONTAINING ZEOLITE AND ITS APPLICATION IN HYDROMERIZATION OF LONG CHAIN N-PARAFFINS

(71) Applicant: BHARAT PETROLEUM CORPORATION LIMITED, Mumbai (IN)

(72) Inventors: Ananth Kishore Kumar Sontyana, Greater Noida (IN); Kuppusamy Munusamy, Greater Noida (IN); Sayanti Ghosh, Greater Noida (IN); Shivanand Mukund Pai, Greater Noida (IN); Lalit Kumar, Greater Noida (IN); Mahesh Wamanrao Kasture, Greater Noida (IN); Bharat Lakshman Newalkar, Greater Noida (IN)

(73) Assignee: BHARAT PETROLEUM CORPORATION LIMITED, Mumbai (IN)

( * ) Notice: Subject to any disclaimer, the term of this patent is extended or adjusted under 35 U.S.C. 154(b) by 0 days.

(21) Appl. No.: 16/300,179

(22) PCT Filed: May 10, 2017

(86) PCT No.: PCT/IB2017/052716
§ 371 (c)(1),
(2) Date: Nov. 9, 2018

(87) PCT Pub. No.: WO2017/195123
PCT Pub. Date: Nov. 16, 2017

(65) Prior Publication Data
US 2019/0176137 A1 Jun. 13, 2019

(30) Foreign Application Priority Data

May 11, 2016 (IN) .............................. 201621016491

(51) Int. Cl.
*B01J 29/70* (2006.01)
*C01B 39/48* (2006.01)
(Continued)

(52) U.S. Cl.
CPC .......... *B01J 29/7484* (2013.01); *B01J 21/04* (2013.01); *B01J 29/7042* (2013.01);
(Continued)

(58) Field of Classification Search
CPC ... C01B 39/48; B01J 29/7042; B01J 29/7484; B01J 29/7684; B01J 37/30; C07C 5/00; C07C 2529/74; C07C 2529/76
See application file for complete search history.

(56) References Cited

U.S. PATENT DOCUMENTS 5,087,785 A * 2/1992 Frank ....................... C07C 5/29
585/446
5,336,478 A * 8/1994 Dwyer ................. B01J 29/7042
423/708

FOREIGN PATENT DOCUMENTS

EP        2248585 A1    10/2010
WO    WO-2019058239 A1 *   3/2019 .............. B01J 23/40

OTHER PUBLICATIONS

Snehalkumar Parmar, et al., "Hydroisomerization of n-hexadecane over Pt/ZSM-22 framework: Effect of divalent cation exchange", Journal of Molecular Catalysis A: Chemical 404-405 (2015), pp. 47-56.
(Continued)

*Primary Examiner* — David M Brunsman
(74) *Attorney, Agent, or Firm* — Ladas & Parry LLP

(57) ABSTRACT

The present invention provides a process for preparing a zeolite by hydrothermal heating of silica precursor and
(Continued)

alumina precursor along with a combination of two structure-directing organic templates, N,N-dimethyl formamide and 1,6-diaminohexane in the presence of an alkali. The use of two structure-directing organic templates, not only reduces the crystallization time but also enables the preparation of more catalytically active ZSM-22 of submicron crystallite size. The present invention also provides a process of preparing a noble metal containing zeolite catalyst for hydroisomerization of long chain n-paraffins.

23 Claims, 2 Drawing Sheets

(51) Int. Cl.
| | |
|---|---|
| *B01J 29/74* | (2006.01) |
| *B01J 37/00* | (2006.01) |
| *B01J 29/76* | (2006.01) |
| *B01J 21/04* | (2006.01) |
| *B01J 35/00* | (2006.01) |
| *B01J 35/10* | (2006.01) |
| *B01J 37/04* | (2006.01) |
| *B01J 37/08* | (2006.01) |
| *B01J 37/30* | (2006.01) |
| *C07C 5/27* | (2006.01) |
| *C10G 45/64* | (2006.01) |

(52) U.S. Cl.
CPC ....... *B01J 29/7684* (2013.01); *B01J 35/0066* (2013.01); *B01J 35/1014* (2013.01); *B01J 35/1019* (2013.01); *B01J 37/0009* (2013.01); *B01J 37/0018* (2013.01); *B01J 37/04* (2013.01); *B01J 37/082* (2013.01); *B01J 37/30* (2013.01); *C01B 39/48* (2013.01); *C07C 5/2708* (2013.01); *C10G 45/64* (2013.01); *B01J 2229/186* (2013.01); *C07C 2521/04* (2013.01); *C07C 2529/74* (2013.01); *C07C 2529/76* (2013.01); *C10G 2300/1011* (2013.01); *C10G 2300/1022* (2013.01)

(56) References Cited

OTHER PUBLICATIONS

Snehalkumar Parmar, et al., "Hydroisomerization of Long Chain n-Paraffins over Pt/ZSM-22: Influence of Si/Al Ratio", Energy & Fuels, American Chemical Society, 2015, 29, pp. 1066-1075.

Stefan Ernst, et al., "Synthesis and Shape-Selective Properties of ZSM-22", Applied Catalysis, vol. 48, No. 1, Mar. 1, 1989, pp. 137-148.

Peter A. Jacobs, Johan A. Martens, Synthesis of High-Silica Aluminosilicate Zeolites, Studies in Surface Science and Catalysis, 3-390 1987 (Chapters VI and VII).

* cited by examiner

METHOD FOR THE SYNTHESIS OF A ZSM-22 ZEOLITE, A METAL CONTAINING ZEOLITE AND ITS APPLICATION IN HYDROMERIZATION OF LONG CHAIN N-PARAFFINS

RELATED APPLICATION

This application is an application under 35 U.S.C. 371 of International Application No. PCT/IB2017/052716 filed on 10 May 2017, which claims the benefit of Indian Application No.: 201621016491 filed 11 May 2016, the entire contents of which are incorporated herein by reference.

FIELD OF THE INVENTION

The present invention relates to the method for preparing a zeolite from a combination of two organic structure-directing organic templates wherein one of them is non-selective for TON (theta one) type zeolite. The present invention also relates to a method of synthesis of a noble metal containing the zeolite. The present invention also relates to the application of said prepared zeolite as a support for the preparation of hydroisomerization catalyst for dewaxing applications.

BACKGROUND OF INVENTION

Zeolites are crystalline aluminosilicates, either of natural or synthetic origin with highly ordered structures. They consist of $SiO_4$ and $AlO_4$ tetrahedra, which are interlinked through shared oxygen atoms to give a three dimensional network. They consist of channels and in some cases cavities. The interior of these channels contain adsorbed water molecules and exchanged alkali metal ions, the latter can be exchanged with other metal cations. These cations compensate for the excess negative charge in the framework resulting from the substitution of aluminum in the lattice. The interior of the pore system, with its atomic-scale dimensions, is the active surface of the zeolites. The inner pore structure depends on the zeolite type, composition, and the cations. Thus, zeolites are represented by the general formula:

$$M_{y/n}[(SiO_2)_x(AlO_2)_y] \cdot zH_2O$$

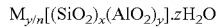

where M is the charge compensating cation with the valency n. M represents the exchangeable cation (eg. alkali or alkaline earth metals or an organic cations). The ratio x/y can have the value 1 to ∞ According to Lowenstein's rule no two aluminum tetrahedras can exist adjacent to one another. The Si/Al molar ratio corresponds to the acid sites in the zeolites. z represents the number of water molecules, which can be reversibly adsorbed in the pores, while y represents the exchange capacity.

Zeolites are also popularly known as 'molecular sieves' due to their ability to differentiate between molecules of different shapes and size. Typically, zeolites have the following properties:

High surface area
Molecular dimensions of the pores
High adsorption capacity
Molecular shape selectivity for reactants/products
Tunable acidity Such unique properties of zeolites have led to their applications in the field of adsorption and catalysis. Today, zeolites have found widespread application as adsorbents, ion exchange materials, detergent builders and catalysts, especially in petroleum refining as Fluidized Catalytic Cracking (FCC) and hydroprocessing catalysts and in the production of petrochemicals.

In the current scenario, due to stringent environmental norms and pressures on refiners to produce clean fuels, hydroprocessing of petroleum feedstocks has become important. Hydroprocessing includes processes that utilize hydrogen to convert petroleum feed stocks to clean and valuable products useful for wide range of applications from transportation fuels to base stocks for lubricating oils. Hydroisomerization is a hydroprocessing route to carry out conversion of n-paraffin to isoparaffin as it offers benefit in terms of product yield. It is routinely practiced for production of motor spirit with desired Research Octane Number (RON), winter grade diesel and Lube Oil Base Stock (LOBS) in oil refineries ["Recent Advances and Future Aspects in the Selective Isomerization of High n-Alkanes, Catalysis Reviews: Science and Engineering, 49:1, 33-139 (2007)"]. The mechanistic aspect of catalysis by hydroisomerization catalysts is discussed in detail in "Fischer-Tropsch Waxes Upgrading via Hydrocracking and Selective Hydroisomerization Oil & Gas Science and Technology—Rev. IFP, Vol. 64, No. 1, 91-112 (2009)".

Skeletal branching of n-alkanes can be achieved using bifunctional zeolite catalysts. According to the bifunctional reaction scheme, the n-alkane is dehydrogenated on the metal and the resulting alkene protonated on the acid site. The alkyl carbenium ion formed upon protonation undergoes skeletal rearrangements and, eventually, cracking through β-scission. β-scission becomes more and more favorable as the branching degree of the carbon chain increases. This explains why on a bifunctional catalyst, the yield of skeletal isomers obtained from an n-alkane when plotted against conversion always exhibits an optimum owing to the occurrence of hydrocracking consecutive to hydroisomerization. Minimization of the hydrocracking reaction is mandatory when high yields of skeletal isomers out of n-alkanes must be achieved. Hence, an ideal balance of metal and acid functions is desired to maximize hydroisomerization. Processes for isomerization of short chain n-paraffin (C6, C8) of gasoline range are performed by employing one of the catalyst systems consisting from group of catalysts such as Chlorinated Pt/Alumina, sulfated zirconia, and Pt/Zeolite and are intended for Research Octane Number (RON) boosting as described in U.S. Pat. No. 4,003,849 and EP 1243332 A1. On the other hand, for long chain n-paraffins (C12 plus) isomerization, medium pore one-dimensional zeolites are found to be potential candidates. Typically, zeolites namely ZSM-23, ZSM-22, ZSM-48, ZSM-12 and SSZ-32 are found to offer ideal options for the targeted application with yield maximization as described in "Studies on Wax Isomerization for Lubes and Fuels, Stud. Surf. Sci. Catal. 84C, 2319-2326". The literature reports mentioned herein above explains the important role of one-dimensional frameworks for isomerization, due to their unique pore geometry which favors the concept of pore-mouth/key-lock catalysis, which is a phenomena occurring on external surface and hence it is required for the aforementioned zeolites to have an submicron crystal size, optimum external surface area in order to obtain higher conversions and isomer selectivities in hydroisomerization reaction as described in the paper Monomethyl-Branching of Long n-Alkanes in the range from Decane to Tetracosane on Pt/H-ZSM-22 Bifunctional Catalyst, J. Catal. 190, 1, 39-48.

Typically, synthesis of one dimensional zeolites namely ZSM-22, -23 is reported in the presence of organic structure directing agent (template) under hydrothermal conditions. The selective templates reported for ZSM-22 synthesis are 1,6-Diaminohexane, 1,8-Diaminooctane, Hexamethylenediamine and N-ethylpyridinium bromide, respectively. On the other hand, ZSM-23 is synthesized using pyrrolidine, Heptamethonium Bromide and Octamethonium Bromide. Recently, attempts have been made to prepare intergrowth of ZSM-22 and -23 using mixed template approaches. The synthesis conditions reported to obtain pure phase of ZSM-22 with desired Si/Al ratio is listed in Table 1. Various catalysts for hydroisomerization based on ZSM-22 zeolite reported in the literature and their performance are summarized in Table 2.

TABLE 1 synthesis conditions and properties of ZSM-22 zeolite reported in literature

| Reference | Template/Silica Source | Crystallization Time/Temperature | Obtained zeolite | Crystallite Size ($\mu m$) | Surface Area/ External surface area ($m^2/g$) |
|---|---|---|---|---|---|
| Shewangizaw Teketel, ACS Catal 2012, 2, P26. | Diaminooctane/ Ludox AS-30 | 3-4 days/160° C. | ZSM-22 | 2-3 | 173/NR |
| M. Zhang, Ind, Eng Chem Res, 2016, 55, P6069. | 1,6-DAH/ fumed silica | 3 days/160° C. | ZSM-22 | 2 | 209/NR |
| Park, App, Cat-A, 2000, 203, p201. | 1,6-DAH/ Ludox HS-30 | 3 days/160° C. | ZSM-22 | NA | 200/NR |
| A. K. Jamil, Micr and Mesopor Mater 2016, 227, p16. | 1,6-DAH/ Colloidal Silica | 2 days/180-200° C. | ZSM-22 | NA | 150/33 |
| RSC advances, 2015, 5, p99201 | 1,6-diaminohexane and Ludox AS40 | 4 days/160° C. | ZSM-22 | 1-2 | 220/NR |

*NR—Not reported

TABLE 2

Catalytic Performance of various hydroisomerization catalysts reported in literature

| Reference | Catalyst Pt (Wt %) on ZSM-22 | Feed | Operating conditions | Conversion (%) | Selectivity (%) |
|---|---|---|---|---|---|
| M. Zhang, Ind, Eng Chem Res, 2016, 55, P6069. | Pt | n-hexadecane | 300° C. and 40 bar | 20 | 30 |
| Park, App. Cat-A, 2000, 203, p201. | Pt(0.5 wt. %) | n-hexadecane | 350° C. and 103 bar | 41 | 31 |
| N. Batalha, Reac Kinet Mech Cat 2012, 107, 285. | Pt(0.7 wt. %) | n-hexadecane | 220° C. and 30 bar | 90 | 83 |
| Y. wang, J. Cat. 2015, 322, p1. | Pt(0.48 wt. %) | n-hexadecane | 270° C., 40 bar and 1 WHSV | 35 | 52 |
| Y. wang, J. Cat. 2015, 322, p1. | Pt(0.49 wt. %) | n-hexadecane | 270° C. 40bar and 1 WHSV | 32 | 72 |
| Y. wang, J. Cat. 2015, 322, p1. | Pt(0.45 wt. %) | n-hexadecane | 270° C., 40bar and 1 WHSV | 30 | 45 |
| Yunfei Bi, RSC Adv, 2015, 5, 99201. | Pt(0.51 wt. %) | n-hexadecane | 288° C. | 78 | 51 |
| Yunfei Bi, RSC Adv, 2015, 5, 99201. | Pt(0.51 wt. %) | n-hexadecane | 290° C. | 85 | 73 |
| Yunfei Bi, RSC Adv, 2015, 5, 99201. | Pt(0.51 wt. %) | n-hexadecane | 296° C. | 88 | 80 |

Based on the literature study, it is apparent that zeolites with surface area (150-220 m2/g) as well as external surface area (>30 $m^2/g$) have been employed successfully for hydroisomerization of long chain n-paraffins. This aspects is so far achieved using single template approach (Table 1) and examples listed below.

Furthermore, literature reports different approaches like employing different templates and silica sources for the zeolite synthesis, adding zeolite seeds to the final gel, using amine/alcohols/diol components along with templates during gel preparation and employing microwave-assisted hydrothermal synthesis to prepare ZSM-22 zeolite. For example, U.S. Pat. No. 4,556,477 describes the synthesis of highly siliceous crystalline ZSM-22 using a reaction mixture consisting of an oxide form of an organic compound containing an element of Group 5-B containing at least one alkyl or aryl group having at least 2 carbon atoms. The inventors have disclosed that, the ZSM-22 zeolite of this invention can be prepared at a relatively wide range of $SiO_2/Al_2O_3$ ratios ranging from 20 to about ∞. The crystallization time for the synthesis of ZSM-22 was 72 hrs and the crystallization temperature was 160° C.

U.S. Pat. No. 5,785,947 describes the synthesis of crystalline zeolites using amine component along with organic template. The inventor has claimed that, by using amine component in the synthesis mixture will reduce the amount of organic template required for the zeolite synthesis. The inventors have also disclosed the synthesis of ZSM-22 zeolite using 2,6-dimethylpiperdine as organic template and isobutyl amine as amine component. The crystallization time for the synthesis of ZSM-22 was 6 days and the crystallization temperature was 170° C.

U.S. Pat. No. 5,866,069 describes the process for preparing ZSM-22 zeolite under static or low rpm conditions. The gel composition of the prepared zeolite was 1.28 $K_2O/3.00$ $R/0.110$ $Al_2O_3/10$ $SiO_2/402$ $H_2O$ using 1,6-diaminohexane (R), potassium hydroxide, aluminum sulfate, $Al_2(SO_4)_3.18H_2O$ and colloidal silica solution (LUDOX AS-40, Sigma-Aldrich) as precursors. The inventors have disclosed that by adding small quantity of seed crystals of ZSM-22 will compensate for insufficient stirring. The inventor has also reported that, the crystallization temperature is an important parameter and it has to be monitored closely to avoid the formation of impurities. The crystallization time for the synthesis of ZSM-22 was 72 hrs and the crystallization temperature was 160° C. and needle-shaped ZSM-22 crystals of 5-15 micron length were obtained.

ACS catalysis, 2, 26-37 (2012), reported the synthesis of ZSM-22 using diaminooctane and Ludox AS-30 as template and silica source, respectively. The crystallization time for the synthesis of ZSM-22 was 3-4 days and the crystallization temperature was 160° C. Obtained ZSM-22 zeolites had needle-shaped crystals of 2-3 micron length.

Recently RSC advances, 5, 99201-99206, (2015), reported the synthesis of ZSM-22 using 1,6-diaminohexane and Ludox AS40 (40 wt % silica) as template and silica source respectively. The crystallization time for the synthesis of ZSM-22 was 4 days. Obtained ZSM-22 zeolites had needle-shaped crystals of 1-2 micron length.

More recently L&EC research, 55, 6069-6078 (2016), reported the synthesis of ZSM-22 using hexamethylenediamine and Fumed silica as template and silica source respectively. The crystallization time for the synthesis of ZSM-22 was 72 hrs and the crystallization temperature was 160° C. Obtained ZSM-22 zeolites had needle-shaped crystals of 2 micron length.

Likewise, few reports have been reported wherein dual template approach has been employed. Typically, template selective for ZSM-22 and ZSM-23 have been used in combination. This has resulted into formation of ZSM-22/-23 intergrowth. For example, Materials Research Bulletin 44, 2258-2261 (2009), reported the novel dual-template strategy for the synthesis of ZSM-23/ZSM-22 intergrowth zeolite. In the above article, the author reported the synthesis of ZSM-23/ZSM-22 intergrowth zeolite with fixed proportion of 60% ZSM-23/409% ZSM-22 using dimethylamine and diethylamine as a dual template system. In this article, the author has reported that, a molar ratio of diethylamine to dimethylamine of 1:24 resulted in an ZSM-23/ZSM-22 intergrowth zeolite when aluminum sulfate was used as aluminum source, whereas, sodium meta-aluminate as aluminum source, resulted in ZSM-23/ZSM-22 intergrowth zeolite with a molar ratio of diethylamine to dimethylamine of 1:12. The author has also claimed that, the molar ratio of diethylamine to dimethylamine was the key factor for the synthesis of intergrowth zeolites.

Microporous Mesoporous Material 132, 54-59 (2010) reported a method of using mixture of structure-directing agent (SDA) molecules to prepare the ZSM-23/ZSM-22 intergrowth. In this study, one template molecule is selective for ZSM-23-type zeolites and the other template molecule alone is selective for ZSM-22-type zeolites. Here, the author has used N-isopropyl-1,3-propanediamine (selective for ZSM-23) and 1-methylbutylamine (selective for ZSM-22) as a dual template system and by varying the ratio of these individual template molecules in the syntheses, the author was able to systematically control the ZSM-23 or ZSM-22 character of the intergrowth product.

Journal of Microporous and Mesoporous Materials 134, 203-209 (2010), brings out a novel synthesis approach for ZSM-23 zeolite using N,N-dimethylformamide (DMF) as template. Using this approach the author was able to produce ZSM-23 at the crystallization temperature ranging from 160-185° C. and crystallization time ranging from 40-96 hr. The author has claimed that, the XRD patterns of the samples produced are in consistent with the reported patterns of MTT zeolite and using this approach ZSM-23 zeolite can be synthesized in a broad range of $SiO_2/Al_2O_3$.

In view of the state of the art discussed hereinabove, it is evident that most of the prior art ZSM-22 zeolite synthesis methods require large crystallization times (>72 hours) and the zeolite prepared using these methods leads to zeolite crystals of more than 2 micron size. However, the above approaches have resulted in higher zeolite synthesis cost, for the synthesis of pure metal containing zeolite particularly ZSM-22 due to increased synthesis time.

Accordingly, there is a need in the art for a fast and cost-effective process for synthesizing pure zeolite (particularly ZSM-22) with reduced crystallite size. The present invention provides an economical process of preparing metal containing zeolite by using precipitated silica source and by employing dual template strategy, which results in pure metal containing (ZSM-22) zeolite with smaller crystals (<1 micron) at less crystallization time. The dual template strategy disclosed in the present invention employs the use of non-selective ZSM-22 template in excess. Furthermore, the process of the present invention results in a metal containing zeolite, ZSM-22 with smaller crystal size, optimal pore structure, external surface area and surface area leading to a hydroisomerization catalyst with good activity and high isomerization selectivity at less severe operating conditions.

Objects of the Present Invention

It is an important object of the present invention to provide a method for preparing a zeolite.

It is another important object of the present invention to provide a methodology for synthesizing pure containing zeolite (particularly ZSM-22).

It is another object of the present invention to provide an economical method of preparing metal containing zeolite by using precipitated silica source and by employing dual template strategy, which results in pure (ZSM-22) zeolite at less crystallization time.

It is yet another object of the present invention to obtain a metal containing zeolite, ZSM-22 with smaller crystal size, and optimal acidity, external surface area and surface area which leads to a hydroisomerization catalyst with high activity and high isomerization selectivity at less severe operating conditions.

SUMMARY OF THE INVENTION

The present invention relates to a method for preparing a zeolite from silica source comprising preparing zeolite support by hydrothermal crystallization of silica and alumina precursors along with a combination of two structure-directing organic templates, N,N-dimethyl formamide and 1,6-diaminohexane in the presence of an alkali to obtain the zeolite.

In one embodiment the present invention provides a method for preparing a zeolite wherein the said Zeolite is ZSM-22.

In yet another embodiment the present invention provides a method for preparing a zeolite wherein said silica precursor is selected from the group consisting of silica sols, tetraalkyl orthosilicates, silicon dioxides such as fumed silicas and precipitated silicas, preferably precipitated silicas.

In still another embodiment the present invention provides a method for preparing a zeolite, wherein said alumina precursor is $Al_2(SO_4)_3.18H_2O$.

In another embodiment the present invention provides a method for preparing a zeolite wherein the mole ratio of organic 1,6-diaminohexane and N,N-dimethyl formamide is in the range of 1:0.1 to 1:10

In yet another embodiment the present invention provides a method for preparing a zeolite wherein the alkali is sodium hydroxide or potassium hydroxide or a mixture of thereof.

In still another embodiment the present invention provides a method for preparing a zeolite wherein the acidic form of zeolite is obtained by using ammonium nitrate.

In another embodiment the present invention provides a method for preparing a zeolite wherein the molar ratio of silica to alumina $SiO_2Al_2O_3$ in the zeolite is not more than 300, preferably in the range of 30 to 150.

In another embodiment the present invention provides a method for preparing a noble metal containing catalyst zeolite comprising the steps: (a) converting the zeolite to its acidic form by ion-exchanging with precursor salts which release ammonia; (b) treating the acidic form with a metal by the process of ion-exchange with a metal precursor salt to obtain noble metal loaded acidic form of the zeolite; (c) drying the metal loaded acidic form of the zeolite to obtain a dried material; (d) extrusion of dried material with a binder selected from the group consisting of clays, silicas, aluminas, metal oxides, and mixtures thereof to obtain an extruded catalyst; and (e) calcining the extruded catalyst under constant air flow to obtain a metal-containing catalyst zeolite.

In yet another embodiment the present invention provides a method for preparing a noble metal containing catalyst zeolite wherein the acidic form in step (*a*) is H form which is obtained by exchanging K+ form of zeolite with ammonium nitrate and followed by calcination.

In still another embodiment the present invention provides a method for preparing a noble metal containing catalyst zeolite wherein said acidic H-form has a surface area in the range of 100-320 m$^2$/gm, preferably more than 220 m$^2$/gm.

In another embodiment the present invention provides a method for preparing a noble metal containing catalyst zeolite wherein said acidic H-form has a crystal size of <1 micron and external surface area in the range of 10-80 m$^2$/gm.

In yet another embodiment the present invention provides a method for preparing a noble metal containing catalyst zeolite wherein the acidic H-form has acidity in the range of 50-300 µmol/gm.

In still another embodiment the present invention provides a method for preparing a noble metal containing catalyst zeolite wherein the step (a and b) are carried out at 550° C.

In another embodiment the present invention provides a method for preparing a noble metal containing catalyst zeolite wherein said metal containing catalyst has metal dispersion over 10 to 95%.

In yet another embodiment the present invention provides a method for preparing a noble metal containing catalyst zeolite wherein the acidic H-form is loaded with Group-VIII metal by ion-exchange using a precursor salt, preferably Platinum salt or palladium salt, more preferably it is platinum.

In still another embodiment the present invention provides a method for preparing a noble metal containing catalyst zeolite wherein said platinum salt used for ion-exchange is tetra-ammonium platinum nitrate complex.

In another embodiment the present invention provides a method for preparing a noble metal containing catalyst zeolite wherein the wt % of platinum in the metal containing catalyst is 0.05-3 wt %, preferably 0.1 to 1.0 wt %.

In yet another embodiment the present invention provides a method for preparing a noble metal containing catalyst zeolite wherein said binder is in the percentage of 30 to 70%, preferably 40-65%.

In still another embodiment the present invention provides a method for preparing a noble metal containing catalyst zeolite wherein in step(d) 30% w/w to 70% w/w of the dried material is extruded with 70% w/w to 30% w/w of binder.

In another embodiment the present invention provides a method for preparing a noble metal containing catalyst zeolite wherein in step(e) calcination of the extruded catalyst is at 250-400° C. under constant air flow.

In yet another embodiment the present invention provides a method for preparing a noble metal containing catalyst zeolite wherein the crystallization temperature is in the range of 130 to 180° C.

In still another embodiment the present invention provides a method for preparing a noble metal containing catalyst zeolite wherein the crystallization time is in range between 10-96 hrs, preferably 24 hrs.

In another embodiment the present invention provides a metal-containing catalyst ZSM-22 zeolite prepared by a method as provided herein.

In yet another embodiment the metal-containing catalyst of ZSM-22 zeolite is a hydroisomerization catalyst for hydroisomerization of $C_{12}$ to $C_{40}$ n-paraffins fraction in hydrocarbon mixture.

In still another embodiment the noble metal containing catalyst zeolite metal-containing catalyst of ZSM-22 zeolite for hydroisomerization catalyst is not limited to Fischer-Tropsch wax, diesel, Bio-Oil and for the production of Microcrystalline wax from slack wax and paraffin wax.

DETAILED DESCRIPTION OF INVENTION

Figure 1:
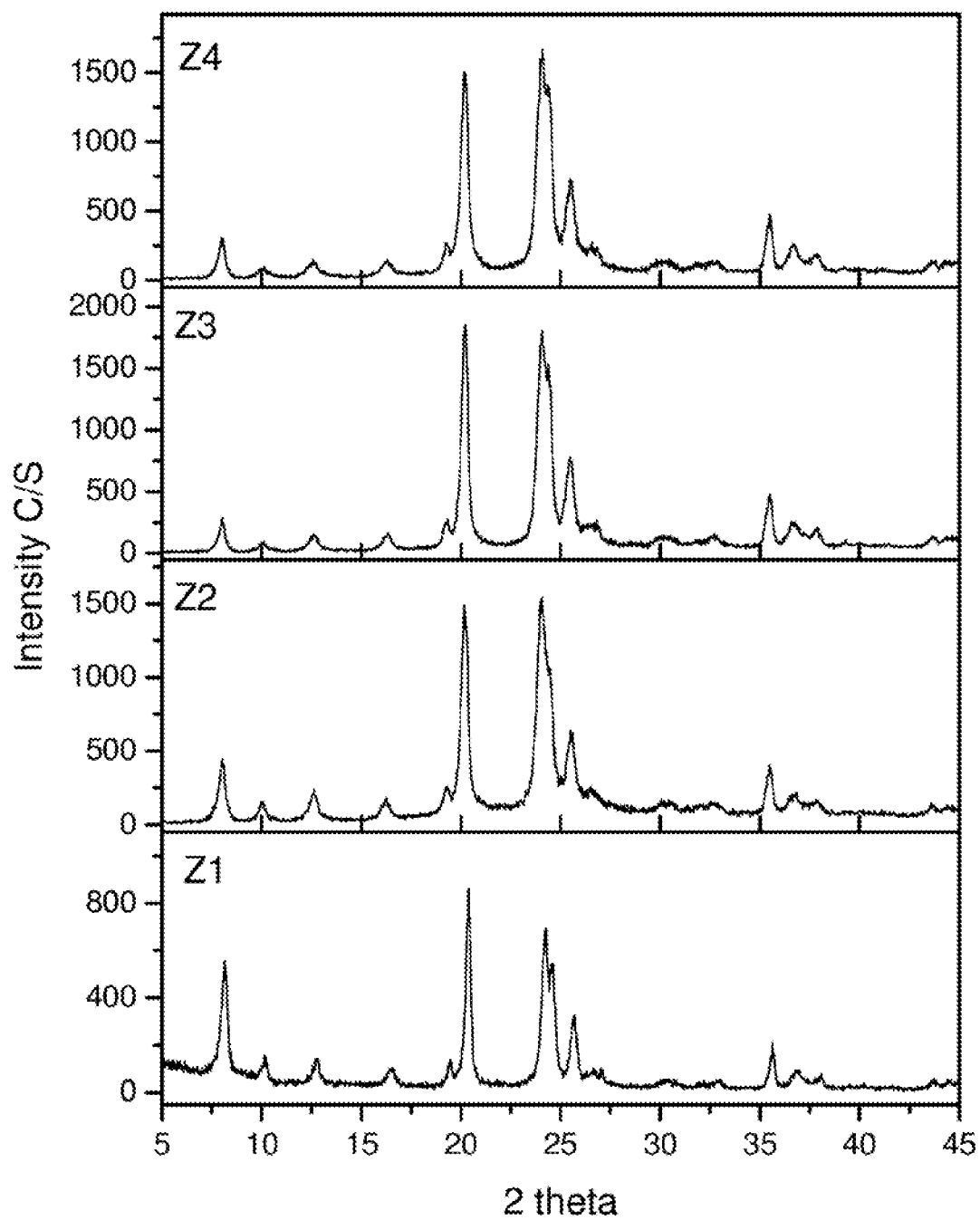
FIG. 1: Powder X-ray Diffraction pattern of ZSM-22 synthesized by employing method as mentioned in Examples 1 to 4.
Figure 2:
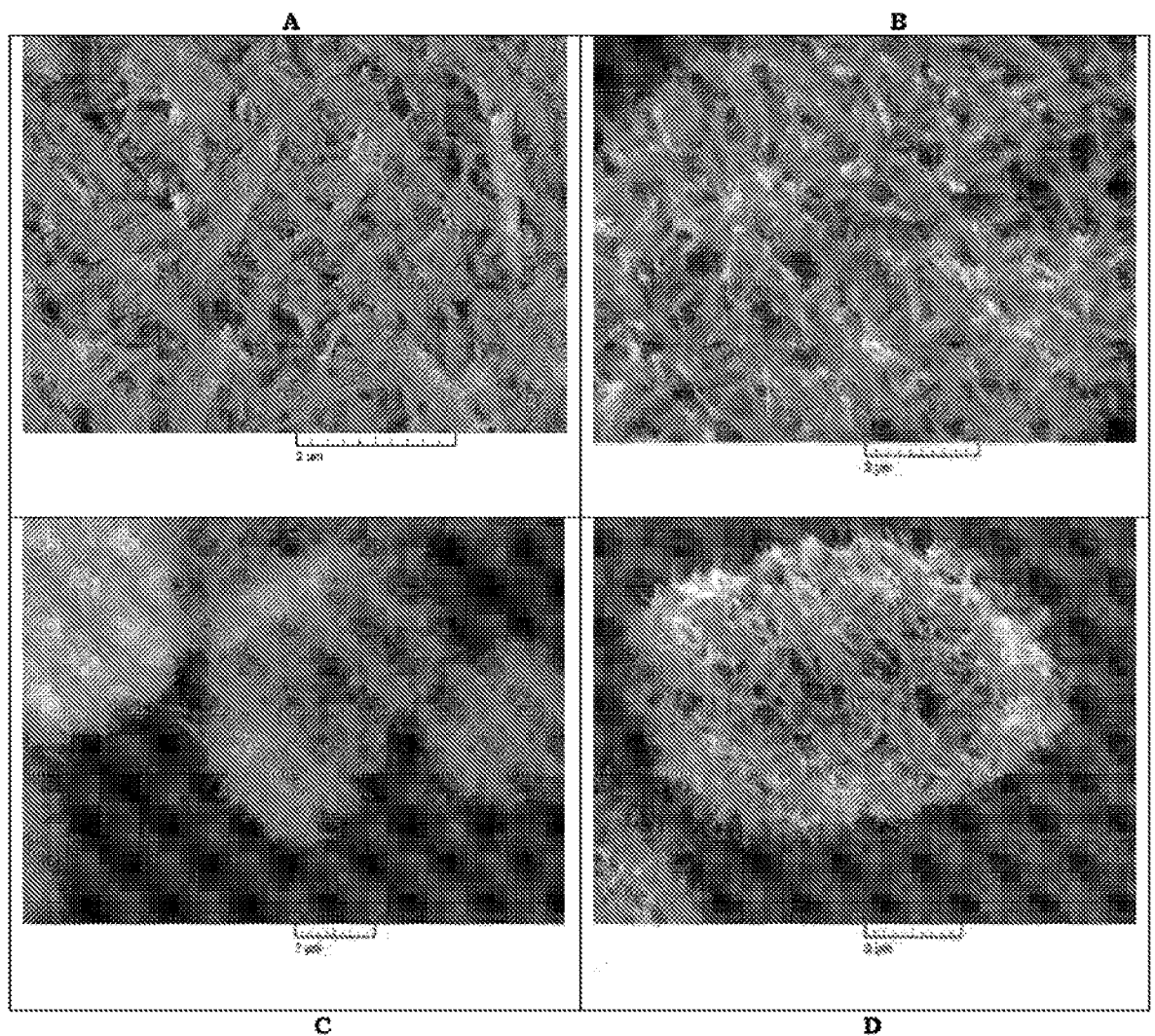
FIG. 2: Scanning Electron Microscope of ZSM-22 zeolite A) Prepared in Example-1 and (B-D) described in Examples-(2-4).

The present invention relates to the method of synthesis of a metal containing zeolite using a combination of two organic structure-directing agents wherein one of them is non-selective for TON (theta one) type zeolite. The present invention also relates to the application of prepared ZSM-22 zeolite as a support for the preparation of hydroisomerization catalyst for dewaxing applications.

The present invention provides a method for preparing a containing zeolite, comprising: synthesis of a pore filled material under hydrothermal conditions using two different structure directing agent; removal of the structure directing agent to obtain a zeolite material; converting the zeolite material to its acidic form using a inorganic precursor salt and calcination thereafter at about 550° C.; incorporating the calcined acidic porous material with a metal to obtain a metal loaded acidic porous material; drying the metal loaded acidic porous material to obtain a dried material; extruding 50% w/w to 95% w/w of the dried material with 5% w/w to 50% w/w of a binder material to obtain a extruded catalyst; and calcining the extruded catalyst at about 250-400° C. under constant air flow to obtain a dispersed metal-containing catalyst having dispersion of over 80%. The present invention further relates to a catalyst for hydroisomerization of long chain n-paraffins ranging from $C_{12}$-$C_{40}$ on the acidic sites loaded at pore mouths.

The present invention describes a method for preparation of a porous material with appropriate number of pore mouths to ensure a good balance of acidic and metallic sites wherein the acidic porous material is selected from the group consisting of zeolite, molecular sieve, amorphous silica-alumina, solid acids and mixtures thereof, preferably selected from the group consisting of ZSM-5, ZSM-22, ZSM-23, ZSM-35, ZSM-48 and SSZ-32. Yet another embodiment of the present invention relates to a method, wherein the acidic porous material is prepared in the manner described herein from a mixture comprising.

(i) a source of silicon
(ii) a source of aluminium;
(iii) a source of monovalent cation; and
(iv) a mixture of organic structure directing agents;

The synthesis is carried out under vigorous stirring in the range of about 100 to 500 rpm.

The present invention relates to a method wherein the organic structure directing agents are removed at high temperature by calcination and then converted to its acidic form by exchanging the alkali metal cation to obtain the ammonium form of the zeolite which when calcined results into corresponding acidic from.

The present invention also relates to method for obtaining metal loaded acidic form of the zeolite by exchanging some of the acidic sites with metal cations by use of certain metal precursor salts. Upon successful loading of metal, the acidic porous material is obtained after filtration and drying. The dried acidic porous material is next combined with the binder material and formed into extrudates.

The present invention further relates to a method, wherein the binder material is selected from the group consisting of clays, silicas, aluminas, metal oxides, and mixtures thereof. The relative proportions of the zeolite and binder material may vary between 50 to 95% of zeolite and about 5 to 50% of binder material. These extrudates are then calcined at 400° C. under constant air or oxygen flow.

The catalyst so obtained has smaller crystal size, higher surface area, external surface area, pore volume and optimum acid/metal balance leading to higher selectivity for isomerisation even at significantly high conversion values when used for hydroisomerization reaction. The catalyst of the present disclosure is used for hydroisomerization of long chain n-paraffins ranging from $C_{12}$-$C_{40}$. A catalyst with an excellent balance of metal/acidic sites is very much desirable for carrying out hydroisomerization reactions and is of prime importance to refining industry. The hydroisomerization method is responsible for the production of high octane gasoline; dewaxed diesel oil, and high quality lube oil with excellent cold flow properties.

Typically, these isomerization reactions are carried out in presence of hydrogen over a bifunctional catalyst. The bifunctional catalyst has a metal component responsible for dehydrogenation/hydrogenation and an acid function for isomerization/cracking. Herein, the metal component is a Group-VIII metal usually platinum or palladium while the acid function is acidic porous material which could be zeolite, molecular sieve, amorphous, silica-alumina or solid acids selected on the basis of required catalyst activity selectivity and hydrocarbon chain length. Medium pore zeolites (ZSM-12, ZSM-22, ZSM-23, ZSM-35, ZSM-48, ZM-57, SSZ-32, SSZ-20, EU-1, EU-13, KZ-1, KZ-2, Theta-1 etc) and molecular sieves (SAPO-11, SAPO-31, SM-3, SM-6 etc) have been widely used for diesel and lube dewaxing applications.

During the n-paraffin hydroisomerization method, the n-paraffin first undergoes dehydrogenation to olefin at metallic site followed by isomerization to branched olefin at zeolite pore-mouth and then hydrogenation to form saturated branched paraffin which is desirable. If the number of acidic sites is very high, it would lead to the hydrocracking of multibranched isomers leading to loss in yields of the desirable products. Herein, the effect of optimum metal/acid sites and presence of pore mouths is described, which is again based on the total and external surface areas of the catalyst samples is shown.

Catalyst was loaded into a fixed bed micro-reactor operated in an upflow mode. Hexadecane feed along with hydrogen was feed to the reactor using a peristaltic pump to maintain a specified weight hourly space velocity (WHSV) and hydrogen to hydrocarbon ratio. The product composition analysis was done using GC-FID results to obtain catalyst selectivity at a desired conversion level.

In another embodiment, the selectivity of the catalyst is defined to be ratio of Cu isomer yield to the n-hexadecane conversion.

The following examples are provided to illustrate the invention and are not to be construed as limiting thereof.

EXAMPLES

Example 1

Method of Preparation of ZSM-22 Zeolite ZSM-22 (Molar ratio of Si/Al=45) was synthesized using 1,6-diaminohexane as a structure directing agent. As per the method, the crystallization of ZSM-22 was performed using gel molar composition of 27NH$_2$ (CH$_2$)$_6$NH$_2$/12K$_2$O/Al$_2$O$_3$/90SiO$_2$/3670 H$_2$O by employing potassium hydroxide, KOH; aluminum sulfate, Al$_2$(SO$_4$)$_3$.18H$_2$O and precipitated silica as precursors. The hydrothermal crystallization of the gel so prepared was carried out at 160° C. under stirred conditions for 24 h. The crystallized samples were filtered, washed several times with deionized water, dried at 110° C. for 24 h, and finally calcined at 550° C. for 12 h in the presence of air.

Comparative Example 1

Method of Preparation of ZSM-22 Zeolite

The synthesis of ZSM-22 with a composition of 100 $SiO_{2/1}$ $Al_2O_3$/30 HDA/4000 $H_2O$/11.6 $Na_2O$ using hexamethylenediamine and Fumed silica as template and silica source respectively as per the procedure disclosed in literature (I&EC research, 55, 6069-6078 (2016)). The crystallization time for the synthesis of ZSM-22 was 72 hrs and the crystallization temperature was 160° C. n-Hexadecane hydroisomerization activity of the catalyst (COMPCAT-1) prepared using the above mentioned ZSM-22 zeolite is shown in Table 4.

Comparative Example 2

Method of Preparation of ZSM-22 Zeolite

The synthesis of ZSM-22 with a composition of 27$NH_2$(CH$_2$)$_6$NH$_2$: 13$K_2O$: 0.82$Al_2O_3$: 91$SiO_2$: 3670$H_2O$ using 1,6-diaminohexane and Ludox AS40 (40 wt % silica) as template and silica source respectively, as per the procedure disclosed in literature (RSC advances, 5, 99201-99206, (2015)). The crystallization time for the synthesis of ZSM-22 was 4 days. n-Hexadecane hydroisomerization activity of the catalyst (COMPCAT-2) prepared using the above mentioned ZSM-22 zeolite is shown in Table 4.

Comparative Example 3

Method of Preparation of ZSM-22 Zeolite

The synthesis of ZSM-22 with a composition of 27$NH_2$(CH$_2$)$_6$NH$_2$: 13$K_2O$: $Al_2O_3$: 91$SiO_2$: 3670$H_2O$ using 1,6-diaminohexane and Ludox AS40 (40 wt % silica) as template and silica source, respectively. The crystallization time for the synthesis of ZSM-22 was 2 days and the crystallization temperature was 160° C. Chemical and textural Properties of obtained zeolite are shown in Table 3 and the n-Hexadecane hydroisomerization activity of the catalyst (COMPCAT-3) prepared using the above mentioned ZSM-22 zeolite is shown in Table 4.

Example 2

Modified Method of Preparation of ZSM-22 Using Dual Templates

ZSM-22 (Molar ratio of Si/Al=45) was synthesized using the procedure as described in Example 1. In this case the templates used were 1,6-diaminohexane and N,N di-methylformamide. As per the method, the crystallization of ZSM-22 was performed using gel molar composition of 27R/12$K_2O$/$Al_2O_3$/90$SiO_2$/3670$H_2O$ by employing potassium hydroxide, KOH; aluminum sulfate, $Al_2(SO_4)_3$.18$H_2O$ and precipitated silica as precursors. Where R is a mixed template consisting of 1,6-diaminohexane and N,N di-methylformamide in the mole ratio of 2:1 respectively. The hydrothermal crystallization of the gel so prepared was carried out at 160° C. under stirred conditions for 24 h. The crystallized samples were filtered, washed several times with deionized water, dried at 110° C. for 24 h, and finally calcined at 550° C. for 12 h in the presence of air.

Example 3

Modified Method of Preparation of ZSM-22 Using Dual Templates

ZSM-22 (Molar ratio of Si/Al=45) was synthesized using the procedure as described in Example 1. In this case the templates used were 1,6-diaminohexane and N,N di-methylformamide. As per the method, the crystallization of ZSM-22 was performed using gel molar composition of 27R/12$K_2O$/$Al_2O_3$/90$SiO_2$/3670$H_2O$ by employing potassium hydroxide, KOH; aluminum sulfate, $Al_2(SO_4)_3$.18$H_2O$ and precipitated silica as precursors. Where R is a mixed template consisting of 1,6-diaminohexane and N,N di-methylformamide in the mole ratio of 1:1 respectively. The hydrothermal crystallization of the gel so prepared was carried out at 160° C. under stirred conditions for 24 h. The crystallized samples were filtered, washed several times with deionized water, dried at 110° C. for 24 h, and finally calcined at 550° C. for 12 h in the presence of air.

Example 4

Modified Method of Preparation of ZSM-22 Using Dual Templates

ZSM-22 (Molar ratio of Si/Al=45) was synthesized using the procedure as described in Example 1. In this case the templates used were 1,6-diaminohexane and N,N di-methylformamide. As per the method, the crystallization of ZSM-22 was performed using gel molar composition of 27R/12$K_2O$/$Al_2O_3$/90$SiO_2$/3670$H_2O$ by employing potassium hydroxide, KOH; aluminum sulfate, $Al_2(SO_4)_3$.18$H_2O$ and precipitated silica as precursors. Where R is a mixed template consisting of 1,6-diaminohexane and N,N di-methylformamide in the mole ratio of 1:3 respectively. The hydrothermal crystallization of the gel so prepared was carried out at 160° C. under stirred conditions for 24 h. The crystallized samples were filtered, washed several times with deionized water, dried at 110° C. for 24 h, and finally calcined at 550° C. for 12 h in the presence of air.

Example 5

Preparation of Acidic Form of Zeolites

All the crystallized samples were filtered, washed several times with deionized water, dried overnight at 110° C. The sample was calcined in air at 550° C. for 12 h. The proton form of the sample was obtained by exchanging the sample three times with ammonium nitrate under reflux at 90° C. for 3-4 h followed by calcination at 550° C. for 4 h. The ZSM-22 samples prepared in Example 1, Example 2, Example 3, and Example 4, are labelled as Z1, Z2, Z3 and Z4 respectively.

Example 6

Characterisation of Zeolite and its Catalysts Sample

All the four zeolites were characterized by several physiochemical techniques. The values are given the table below.

TABLE 3

Textural properties of the all the zeolites samples

| Sample | BET surface area (m$^2$/g) | Micropore surface area (m$^2$/g) | External surface area (m$^2$/g) | Pore volume (cc/g) | Acidity (μmol/gm) |
| --- | --- | --- | --- | --- | --- |
| Z1 | 154 | 103 | 51 | 0.146 | 218 |
| Z2 | 230 | 185 | 45 | 0.149 | 183 |
| Z3 | 270 | 222 | 47 | 0.179 | 162 |
| Z4 | 226 | 176 | 50 | 0.158 | 131 |

TABLE 3-continued

Textural properties of the all the zeolites samples

| Sample | BET surface area (m²/g) | Micropore surface area (m²/g) | External surface area (m²/g) | Pore volume (cc/g) | Acidity (μmol/gm) |
|---|---|---|---|---|---|
| Cooperative example 3 | 197 | 151 | 46 | 0.060 | 171 |

Example 7

Pt Loading, Binding and Extruding of the ZSM-22 Zeolite Catalyst

The proton form of the above sample was used to make extruded Pt-loaded catalyst. 0.05 g of tetra-ammonium platinum nitrate complex was dissolved in 50 ml of distilled water. This solution was taken into a flask and 3.5 g of H-ZSM-22 was added on to it. The pH of the solution was adjusted to be maintained in the range of 9 to 10 using tetra butyl ammonium hydroxide. The product was filtered and dried at 100° C. 50 parts of Pt/I-ZSM-22 crystal were mixed with 50 parts of pseudoboehmite alumina binder in a muller. Sufficient amount of 5% acetic acid was added to produce an extrudable dough type mass on a 1" diameter extruder. This dough was extruded into ¹⁄₁₆" diameter cylindrical extrudates and then dried in an oven at 130° C. overnight. The dried extrudate was calcined in oxygen at 400° C. Four catalyst samples were prepared and coded as CAT-1 (prepared using zeolite Z1), CAT-2 (prepared using zeolite Z2), CAT-3 (prepared using zeolite Z3) and CAT-4 (prepared using zeolite Z4) respectively and the final catalyst composition is shown below:

| Component | Weight % |
|---|---|
| Zeolite | 49.85% |
| Binder | 49.85% |
| Platinum | 0.3% |

Example 8

Measurement of Activity and Selectivity for the Prepared Catalyst

All the catalyst recipes were tested for hydroisomerization selectivity using n-hexadecane as the model feed. 5 g of calcined catalyst extrudate diluted with inert material (quartz) was packed in a stainless steel fixed bed reactor. The catalyst was then dried overnight at 130° C. under nitrogen flow and reduced at 320° C. under a constant $H_2$ flow of 100 ml/min at 60 bar pressure for 5 h. After reduction of the metal, the catalyst was used for hexadecane isomerization reaction. The reaction was carried out at a temperature range of 280-320° C., WHSV of 0.8-1.2 $h^{-1}$, with $H_2$/HC ratio of 600 at 60 bar pressure. The activity and selectivity data for different catalysts are tabulated in the Table 4.

TABLE 4

Comparison of activity and selectivity of different catalysts for n-$C_{16}$ hydroisomerization at similar n-$C_{16}$ conversion

| Sample | Reaction Temperature (° C.) | Hexadecane Conversion (%) | Isomerization Selectivity (%) | Yield of isomers (%) |
|---|---|---|---|---|
| CAT-1 | 305 | 90.9 | 84.3 | 76.6 |
| COMPCAT-1 | 300 | 20 | 36 | 7.20 |
| COMPCAT-2 | 310 | 80 | 65 | 52 |
| COMPCAT-3 | 305 | 89.1 | 79.3 | 70.5 |
| CAT-2 | 307 | 90.8 | 84.5 | 76.7 |
| CAT-3 | 300 | 90.8 | 87.1 | 79.1 |
| CAT-4 | 305 | 90.6 | 86.3 | 78.3 |

Table 4 shows a comparative analysis of CAT-1, CAT-2, CAT-3 and CAT-4 based on their n-$C_{16}$ hydroisomerization performance vis-à-vis prior art catalysts. All the prepared catalyst showed, performance better than the prior art catalysts. CAT-2, CAT-3, and CAT-4, prepared using dual template strategy showed better performance than the catalyst prepared using single template i.e. CAT-1. Out of all dual template catalyst, CAT-3 prepared using 1,6-diaminohexane and N,N di-methylformamide in the mole ratio of 1:1 as template and precipitated as silica source gave better activity and higher yield for isomers. Superior performance of CAT-3 for n-$C_{16}$ hydroisomerization is attributed to its smaller zeolite crystal size, better surface area, higher external surface area and moderate acidity. In addition to this, CAT-3 required lower operating temperature to achieve given conversion of n-$C_{16}$. Furthermore, a higher requirement of operating temperature during start of run condition is indicative of an overall reduced catalyst life span. These experiments clearly elicit the advantage of using precipitated silica as silica source and dual template strategy for ZSM-22 synthesis.

Although the subject matter has been described herein with reference to certain preferred embodiments thereof, other embodiments are possible. As such, the spirit and scope of the appended claims should not be limited to the description of the preferred embodiment contained therein. Furthermore, precise and systematic details on all above aspects are currently being made. Work is still underway on this invention. It will be obvious to those skilled in the art to make various changes, modifications and alterations to the invention described herein. To the extent that these various changes, modifications and alterations do not depart from the scope of the present invention, they are intended to be encompassed therein.

We claim:

1. A process for the synthesis of zeolite from a reaction mixture comprising silica and alumina precursors along with a combination of two structure-directing organic templates, N,N-dimethyl formamide and 1,6-diaminohexane in the presence of an alkali and maintaining said reaction mixture at a sufficient temperature to crystallize the zeolite and recovering the zeolite wherein the zeolite is selected from zeolites of the TON framework structure.

2. The process as claimed in claim 1, wherein the zeolite is ZSM-22.

3. The process as claimed in claim 1, wherein said silica precursor is selected from the group consisting of silica sols, tetraalkyl orthosilicates, silicon dioxides such as fumed silicas and precipitated silicas.

4. The process as claimed in claim 1, wherein said alumina precursor is $Al_2(SO_4)_3 \cdot 18H_2O$.

5. The process as claimed in claim 1, wherein the mole ratio of organic 1,6-diaminohexane and N,N-dimethyl formamide is in the range of 1:0.1 to 1:10.

6. The process as claimed in claim 1, wherein the alkali is sodium hydroxide, potassium hydroxide or combination thereof.

7. The process as claimed in claim 1, wherein the molar ratio of $SiO_2/Al_2O_3$ in the zeolite is not more than 300.

8. The process as claimed in claim 1, further comprising preparing a noble metal containing zeolite catalyst comprising the steps:
   (a) calcining the zeolite at sufficient temperature to decompose the organic templates;
   (b) converting the zeolite to its acidic form by ion-exchanging with ammonium nitrate and followed by calcination at sufficient temperature to decompose ammonium ions;
   (c) treating the acidic form with a metal by the process of ion-exchange with a metal precursor salt to obtain noble metal loaded acidic form of the zeolite;
   (d) drying the metal loaded acidic form of the zeolite to obtain a dried material;
   (e) extruding the dried material with a binder selected from the group consisting of clays, silicas, aluminas, metal oxides, and mixtures thereof to obtain an extruded catalyst; and
   (f) calcining the extruded catalyst under constant air flow to obtain a metal-containing zeolite catalyst.

9. The process as claimed in claim 8, wherein the acidic form in step (a) is H form which is obtained by exchanging Na+ or K+ or combination of both forms of zeolite with ammonium nitrate and followed by calcination.

10. The process as claimed in claim 9, wherein said acidic H-form has a surface area in the range of 100-320 $m^2/gm$.

11. The process as claimed in claim 9, wherein said acidic H-form zeolite has a crystal size of <1 micron.

12. The process as claimed in claim 9, wherein said acidic H-form has external surface area in the range of 10-80 $m^2/gm$.

13. The process as claimed in claim 9, wherein the acidic H-form has acidity in the range of 50-300 µmol/gm.

14. The process as claimed in claim 8, wherein the steps (a and b) are carried out at 550° C.

15. The process as claimed in claim 8, wherein said metal containing catalyst has metal dispersion over 10 to 95%.

16. The process as claimed in claim 8, wherein the acidic H-form is loaded with Group-VIII metal by ion-exchange using a precursor salt.

17. The process as claimed in claim 16, wherein said platinum salt used for ion-exchange is tetra-ammonium platinum nitrate complex.

18. The process as claimed in claim 16, wherein the wt % of platinum in the metal containing catalyst is 0.05-3 wt %.

19. The process as claimed in claim 8, wherein said binder is in the percentage of 30 to 70%.

20. The process as claimed in claim 8, wherein in step(e) 30% w/w to 70% w/w of the dried material is extruded with 70% w/w to 30% w/w of binder.

21. The process as claimed in claim 8, wherein in step(f) calcination of the extruded catalyst is at 250-400° C. under constant air flow.

22. The process according to claim 1, wherein the crystallization temperature is in the range of 130 to 180° C.

23. The process according to claim 1, wherein the crystallization time is in range between 10-96 hrs.

* * * * *